US00PP07813P

United States Patent [19]

McKenzie, deceased et al.

[11] Patent Number: Plant 7,813

[45] Date of Patent: Mar. 3, 1992

[54] APPLE TREE NAMED 'SCIGLO'

[76] Inventors: Don McKenzie, deceased, late of Havelock North; by Joy McKenzie, personal representative, P.O. Box 8345, Havelock North; Allan G. White, R D 2, Hastings, all of New Zealand

[21] Appl. No.: 566,283

[22] Filed: Aug. 13, 1990

[51] Int. Cl.[5] ..... A01H 5/00

[52] U.S. Cl. ..... Plt./34

[58] Field of Search ..... Plt./34

[56] References Cited

U.S. PATENT DOCUMENTS

P.P. 2,460 12/1964 Roberts ..... Plt. 34

P.P. 3,637 10/1974 McKenzie ..... Plt. 34

*Primary Examiner*—James R. Feyrer

*Attorney, Agent, or Firm*—Quarles & Brady

[57] ABSTRACT

The new and distinct variety is a selection from a population of seedlings derived from crossing the apple variety known as Splendour (U.S. Plant Pat. No. 2,460) and Gala (U.S. Plant Pat. No. 3,637). The fruit of the apple tree of this new variety has an attractive appearance characterized by its bright red color. The new variety has been named "Sciglo".

1 Drawing Sheet

SUMMARY OF THE INVENTION

The new variety was selected from a population of seedlings derived from crossing the apple variety Splendour (U.S. Plant Pat. No. 2,460) with the apple variety Gala (U.S. Plant Pat. No. 3,637) in 1983. The new variety was distinguishable from the parent varieties Splendour and Gala and also distinguishable from the varieties Sciray, Sciros and Scieur (subject of co-pending applications filed on even date herewith by the same applicants). The features which distinguish the new variety from the aforementioned varieties are:

Gala: Darker colour, more conical shape, later maturity, more aromatic flavour.

Splendour: Earlier maturity, smaller size, darker colour, conical shape, striped colour pattern.

Sciray: Smaller size, earlier maturity, darker striped colour pattern, higher aroma, more conical shape.

Sciros: Earlier maturity, dark striped colour pattern, smaller fruit size, more conical shape.

Scieur: Earlier maturity, darker striped colour pattern, conical shape, sweeter flavour.

The new variety has been named the "Sciglo" variety. Asexual propagation by budding shows that the unique combination of characteristics and distinct colour come true to form and are established and transmitted through succeeding propagations.

BRIEF DESCRIPTION OF THE DRAWINGS

The accompanying drawings show typical specimens of the foliage and fruit of the new variety as depicted in colours as nearly true as is reasonably possible to make the same in a colour illustration of this character.

View A is a side view of an apple of the variety.

View B is a bottom view of an apple of the variety.

View C is a cross-sectional view of an apple of the variety.

View D is a top view of an apple of the variety.

Figure 1:
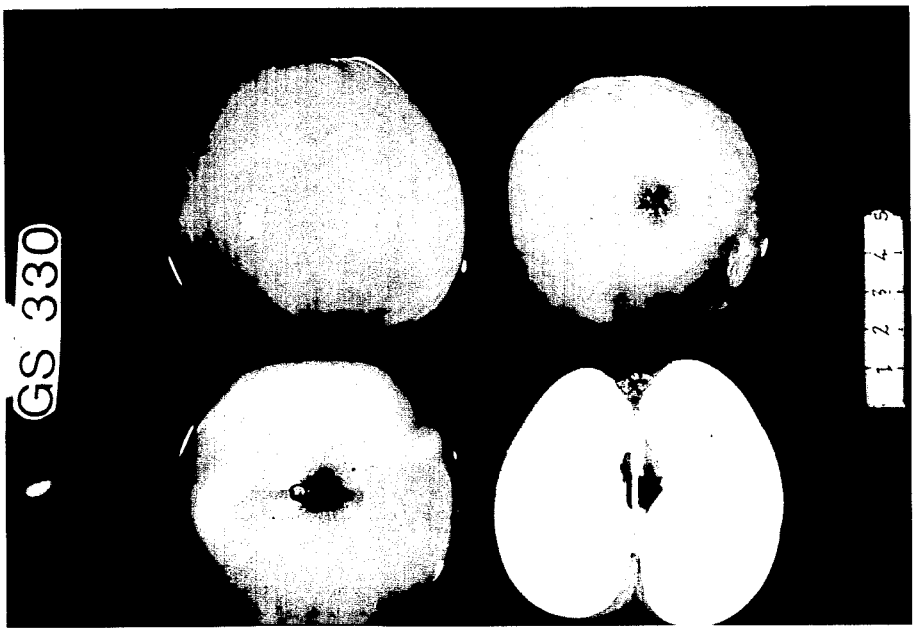
FIG. 1 represents four views of the apple. Beginning in the upper right corner and proceeding clockwise.
Figure 2:
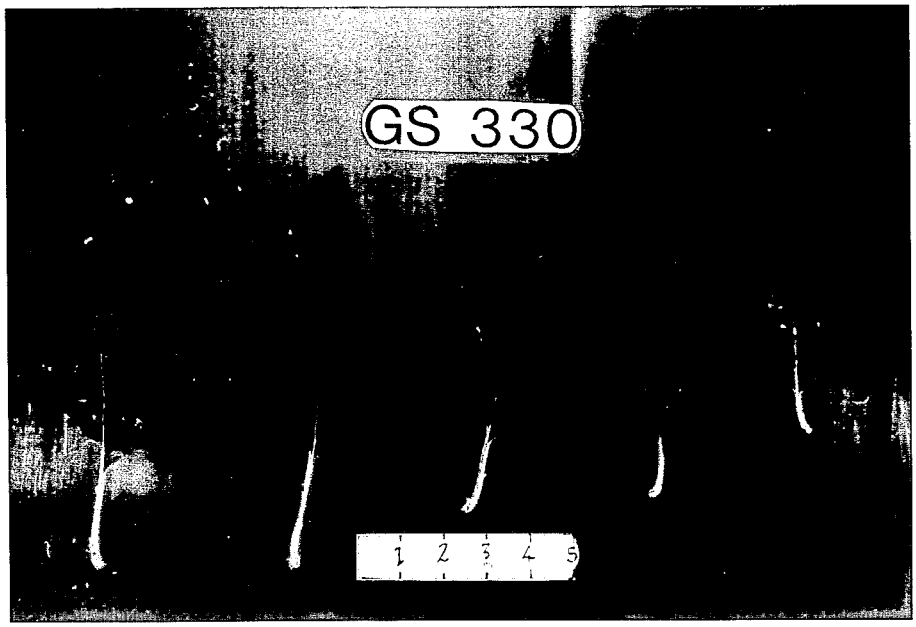

FIG. 2 is a view showing five leaves of the variety.

DETAILED DESCRIPTION OF THE DISCLOSURE

The following is a detailed description of the new variety with color terminology in accordance with the Royal Horticultural Society Colour Chart (R.H.S.C.C.) except where general color terms of ordinary meaning are used as is clear from the context.

The specimens described were grown at Havelock North, New Zealand. The observations were made in the 1989 season on trees which were three years old at the time.

The fruit ripened for eating towards mid-season. Specifically harvest commences about February 15 and ends about March 5 in New Zealand. The trees flowered commencing about October 12 and were in full bloom occurs by October 20 in New Zealand.

Trees: Medium-large; spreading habit; bearing, on spurs; vigor medium with annual growth for eight year old trees with MM106 rootstock being about 400 mm; spurs occurring at a rate of 3 per 10 cm. on three year old growth.

Trunk: Smooth, size, large; the bark is RHSCC 176A when new and RHSCC 201C when old.

Branches: Moderately thick; smooth; multibranching; the angle of branching being commonly 25 degrees above the horizontal; the spread-to-height ratio being about 1 to 1.5.

Lenticels: Average; small.

Leaves:

*Length.*—3¼ inches.

*Width.*—1 6/8 inches; medium size; upward pose; medium length/width ratio of blades; concave to straight shape in cross section; serrate indentation of margin; medium glossiness of upper sides; medium pubescence on lower side; medium petiole length; medium stipule size; medium time of bud burst; the color of the blade is RHCSS 137C, the stems are RHSCC 163C and 182B, and the veins are RHSCC 160C.

Flowers: Medium time of beginning of flowering (10% flowers); medium size; flat shape; margins of petals touching; colour of bud just before flower opens, pink.

Fruit: Examined at peak maturity.

*Soluble solids.*—14.42.

*Size.*—Medium; axial diameter, 2¼ inches; transverse diameter 2½ inches.

*Shape.*—Uniform; medium to long conical; symmetrical in side view; ribbing present; medium crowning at distal end.

*Cavity.*—Medium depth; medium width.

*Basin.*—Shallow to medium depth; medium to broad width; ribbing present.

*Stem.*—Medium thickness (comparable to Cox's Orange Pippin); long length (comparable to Red Delicious).

*Calyx.*—Closed; calyx tube length, short; calyx tube width, medium; calyx tube shape, Y shaped.

*Sepal.*—Length, long; spacing, touching.

*Eye.*—Size, medium; aperture, open.

*Skin.*—Medium-thick; smooth; bloom of skin, present; greasiness of skin, present; cracking tendency of skin, absent; background colour, yellow-green RHSCC 10B.

*Over-colour.*—Approximately eighty percent of over-colour of skin; red RHSCC 46A; solid flush; weak russet about stem cavity.

*Flesh.*—Juicy; firm; cream; crisp, melting; Penetrometer equals 8.25 kg.

*Texture.*—Fine.

*Flavour.*—Strong sweetness; medium acidity (pH about 4.06); sweet with acid balance; similar acid than Gala, more aromatic than Gala.

*Weight of fruit.*—150 gm.

*Quality.*—Excellent.

*Core.*—Distinctness of coreline in cross section (median through locules), weak; aperture of locules in cross-section, open; central cavity (in cross section) absent.

*Sinus.*—Closed.

*Seeds.*—Five locules; 8 to 10 seeds total, 2 seeds per locule maximum; seed length 8 mm.; seed width 4 mm.; form obtuse; color RHSCC 200B.

Use: Market; dessert.

Keeping quality: Very good; no disorders after 98 days.

Resistance to:

*Insects.*—Good.

*Diseases.*—Good.

Production: Early and regular cropping.

Growth habit: Standard, fruit bourne on short spurs.

Management: Trees require pruning in winter and fruit thinning in early summer. Trees in test plot trained as center leader trees. Natural habit is a rounded crown with many branches.

It is claimed:

1. A new and distinct variety of apple tree which is selected from seedlings derived from a cross of the apple variety Gala (U.S. Plant Pat. No. 3,637) and Splendour (U.S. Plant Pat. No. 2,460) substantially as shown and described characterized by its overall bright red colour and sweet flavour.

* * * * *